United States Patent [19]

Bourrain et al.

[11] Patent Number: 6,127,388

[45] Date of Patent: Oct. 3, 2000

[54] AZETIDINE, PYRROLIDINE AND PIPERIDINE DERIVATIVES AS 5-HT$_{1D}$ RECEPTOR AGONISTS

[75] Inventors: Sylvie Bourrain, Harlow; Angus Murray MacLeod, Bishops Stortford; Graham Andrew Showell, Welwyn Garden City; Leslie Joseph Street, Harlow, all of United Kingdom

[73] Assignee: Merck Sharp & Dohme Ltd., Hoddesdon, United Kingdom

[21] Appl. No.: 09/171,929

[22] PCT Filed: May 15, 1997

[86] PCT No.: PCT/GB97/01330

§ 371 Date: Oct. 26, 1998

§ 102(e) Date: Oct. 26, 1998

[87] PCT Pub. No.: WO97/45426

PCT Pub. Date: Dec. 4, 1997

[30] Foreign Application Priority Data

May 24, 1996 [GB] United Kingdom .................... 9610979

[51] Int. Cl.⁷ .......................... A61K 31/443; A61P 25/06; C07D 405/14
[52] U.S. Cl. .................... 514/337; 546/276.4; 546/278.4; 546/279.1
[58] Field of Search .................... 514/337; 546/276.4, 546/278.4, 279.1

[56] References Cited

FOREIGN PATENT DOCUMENTS

WO 94/08993 4/1994 WIPO .
WO 95/28400 10/1995 WIPO .
WO 95/32196 11/1995 WIPO .
WO 96/04274 2/1996 WIPO .

*Primary Examiner*—Patricia L. Morris
*Attorney, Agent, or Firm*—James L. McGinnis; David L. Rose

[57] ABSTRACT

A class of substituted azetidine, pyrrolidine and piperidine derivatives of Formula I are selective agonists of 5-HT$_1$-like receptors, being potent agonists of the human 5-HT$_{1D\alpha}$ receptor subtype whilst possessing at least a 10-fold selective affinity for the 5-HT$_{1D\alpha}$ receptor subtype relative to the 5-HT$_{1D\beta}$ subtype; they are therefore useful in the treatment and/or prevention of clinical conditions, in particular migraine and associated disorders, for which a subtype-selective agonist of 5-HT$_{1D}$ receptors is indicated, whilst eliciting fewer side-effects, notably adverse cardiovascular events, than those associated with non-subtype-selective 5-HT$_{1D}$ receptor agonists.

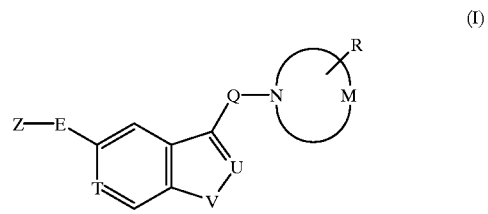

5 Claims, No Drawings

AZETIDINE, PYRROLIDINE AND PIPERIDINE DERIVATIVES AS 5-HT$_{1D}$ RECEPTOR AGONISTS

The present invention relates to a class of substituted azetidine, pyrrolidine and piperidine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D\alpha}$ and 5-HT$_{1D\beta}$ receptor subtypes (cf. WO-A-91/17174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf. G. W. Rebeck et al., *Proc. Natl. Acad. Sci. USA*, 1994, 91, 3666–9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT$_{1D}$ receptor agonists.

WO-A-94/08993 and WO-A-95/28400 describe substituted pyridinyl-benzofuran derivatives, and analogues thereof. These compounds are stated therein to be selective agonists at 5-HT$_1$-like receptors and thus useful in treating conditions associated with cephalic pain, including migraine. Neither of these publications, however, discloses or even suggests the substituted azetidine, pyrrolidine and piperazine derivatives provided by the present invention.

Moreover, nowhere in the prior art mentioned above is there any disclosure of a subtype-selective 5-HT$_{1D}$ receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

WO-A-95/32196, WO-A-96/04269 and WO-A-96/04274 describe various classes of heterocyclic compounds as alpha subtype-selective agonists of the human 5-HT$_{1D}$ receptor. However, there is no disclosure or suggestion in any of these publications of the substituted six-membered heteroaromatic ring-containing compounds provided by the present invention.

The compounds according to the present invention are subtype-selective 5-HT$_{1D}$ receptor agonists having a human 5-HT$_{1D\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D\alpha}$ receptor subtype relative to the 5-HT$_{1D\beta}$ subtype. Moreover, the compounds in accordance with this invention possess interesting properties in terms of their efficacy and/or bioavailability.

The present invention provides a compound of formula I, or a salt or prodrug thereof:

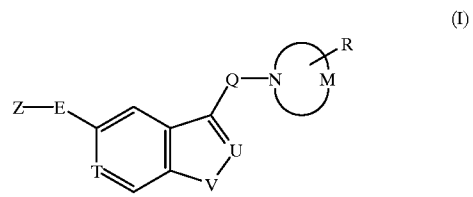

(I)

wherein

Z represents an optionally substituted six-membered heteroaromatic ring selected from pyridine, pyrazine, pyrimidine and pyridazine;

E represents a chemical bond or a straight or branched alkylene chain containing from 1 to 4 carbon atoms;

Q represents a straight or branched alkylene chain containing from 1 to 4 carbon atoms, optionally substituted in any position by one or more substituents selected from fluoro and hydroxy;

T represents nitrogen or CH;

U represents nitrogen or C—R$^2$;

V represents oxygen, sulphur or N—R$^3$;

R$^2$ and R$^3$ independently represent hydrogen or C$_{1-6}$ alkyl;

M represents the residue of an azetidine, pyrrolidine or piperidine ring;

R represents a group of formula —W—R$^1$;

W represents a chemical bond or a straight or branched alkylene chain containing from 1 to 4 carbon atoms, optionally substituted in any position by a hydroxy group;

R$^1$ represents —OR$^x$, —SR$^x$, —SOR$^x$, —SO$_2$R$^x$ or —NR$^x$R$^y$; and

R$^x$ and R$^y$ independently represent hydrogen, hydrocarbon or a heterocyclic group; or R$^x$ and R$^y$ together represent a $C_{2-6}$ alkylene group, which alkylene group may be optionally substituted by one or more substituents selected from $C_{1-6}$ alkyl, aryl and hydroxy, or fused with a phenyl ring.

The six-membered heteroaromatic ring Z in the compounds of formula I above may be optionally substituted by one or more substituents, typically by one or two substituents. Examples of suitable substituents on the six-membered heteroaromatic ring Z include $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, halogen, halo($C_{1-6}$)alkyl, cyano, cyano($C_{1-6}$)alkyl, trifluoromethyl, and —$(CH_2)_a$—$R^4$, in which a is zero, 1, 2 or 3 (preferably zero or 1) and $R^4$ represents —$OR^a$, —$OCOR^c$, —$OCO_2R^a$, —$SR^a$, —$SOR^a$, —$SO_2R^c$, —$CH=CHSO_2R^c$, —$SO_2NR^aR^b$, —$CH=CHSO_2NR^aR^b$, —$NR^aR^b$, —$NR^aCOR^c$, —$NR^aCO(CH_2)_bOR^d$ (in which b is 1 or 2, preferably 1), —$NR^aCO_2R^d$, —$NR^aSO_2R^c$, —$NR^dCONR^aR^b$, —$NR^dSO_2NR^aR^b$, —$COR^c$, —$CH=CHCOR^c$, —$CO_2R^a$, —$CONR^aR^b$, —$CH=CHCONR^aR^b$, or —$CONR^dNR^aR^b$, or $R^4$ represents a group of formula (a), (b), (c), (d) or (e):

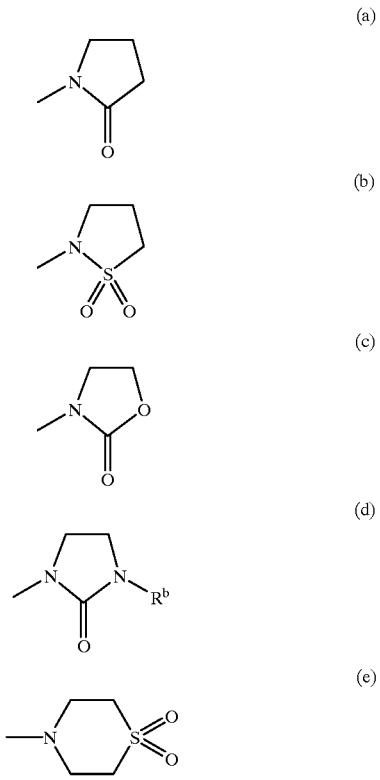

wherein $R^a$ and $R^d$ independently represent hydrogen, $C_{1-6}$ alkyl, trifluoromethyl, phenyl, fluorophenyl or tetrahydropyranyl; $R^b$ represents hydrogen, $C_{1-6}$ alkyl, trifluoromethyl, phenyl or fluorophenyl; and $R^c$ represents hydrogen, $C_{1-6}$ alkyl, trifluoromethyl, phenyl, fluorophenyl, tetrahydropyranyl, azetidinyl, pyrrolidinyl, piperidinyl or morpholinyl.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, indanyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of $C_{3-7}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —$NR^vR^w$, —$NR^vCOR^w$, —$NR^vCO_2R^w$, —$NR^vSO_2R^w$, —$CH_2NR^vSO_2R^w$, —$NHCONR^vR^w$, —$CONR^vR^w$, —$SO_2NR^vR^w$ and —$CH_2SO_2NR^vR^w$, in which $R^v$ and $R^w$ independently represent hydrogen, $C_{1-6}$ alkyl, aryl or aryl ($C_{1-6}$)alkyl, or $R^v$ and $R^w$ together represent a $C_{2-6}$ alkylene group.

When $R^x$ and $R^y$, or $R^v$ and $R^w$, together represent a $C_{2-6}$ alkylene group, this group may be an ethylene, propylene, butylene, pentamethylene or hexamethylene group, preferably butylene or pentamethylene.

When $R^x$ and $R^y$ together represent a $C_{2-6}$ alkylene group, this group may be unsubstituted or substituted by one or more substituents selected from $C_{1-6}$ alkyl, aryl and hydroxy. Typical substituents include methyl, phenyl and hydroxy.

Furthermore, when $R^x$ and $R^y$ together represent a $C_{2-6}$ alkylene group, this group may optionally be fused with a phenyl ring. In this context, a typical group of formula —$NR^xR^y$ as defined for the substituent $R^1$ is 1,2,3,4-tetrahydroisoquinolinyl.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Certain compounds according to the present invention may be capable of existing as tautomeric forms. For example, a hydroxypyridine derivative in accordance with the invention may exist in admixture with its tautomeric pyridone isomer. It is to be understood that all possible tautomers and mixtures thereof in any proportion are encompassed within the scope of the present invention.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In particular, where M represents the residue of a pyrrolidine ring, and the substituent R is attached to the 2-position thereof, then the absolute stereochemical configuration of the carbon atom at the point of attachment of the moiety R is preferably as depicted in structure IA as follows:

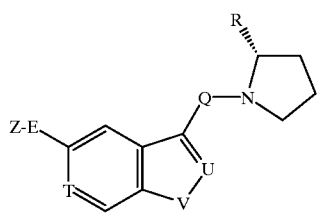

(IA)

wherein Z, E, Q, T, U, V and R are as defined above.

Moreover, where M represents the residue of a pyrrolidine ring, and the substituent R is attached to the 3-position thereof, then the absolute stereochemical configuration of the carbon atom at the point of attachment of the moiety R is preferably as depicted in structure IB as follows:

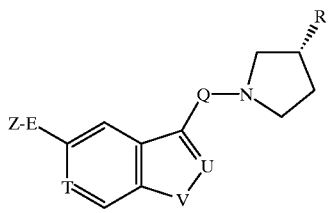

(IB)

wherein Z, E, Q, T, U, V and R are as defined above.

The optionally substituted six-membered heteroaromatic ring Z in formula I is suitably a pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl or pyridazin-4-yl ring, especially pyridin-3-yl or pyrimidin-5-yl.

The six-membered heteroaromatic ring Z is unsubstituted or substituted by one or more substituents, typically by one or two substituents. Examples of optional substituents which may typically be attached to the moiety Z include methyl, methoxy, methoxycarbonyl, methoxymethyl, aminomethyl, dimethylaminomethyl, acetylaminomethyl, benzoylaminomethyl, tert-butoxycarbonylaminomethyl, methylsulphonylaminomethyl, phenylsulphonylaminomethyl, aminocarbonylmethyl, ethyl, aminoethyl, acetylaminoethyl, benzoylaminoethyl, methoxycarbonylaminoethyl, ethoxycarbonylaminoethyl, tert-butoxycarbonylaminoethyl, methylsulphonylaminoethyl, aminocarbonylaminoethyl, methylaminocarbonylaminoethyl, tert-butylaminocarbonylaminoethyl, phenylaminocarbonylaminoethyl, pyrrolidinylcarbonylaminoethyl, cyclopropyl, phenyl, naphthyl, benzyl, phenylethyl, phenylpropyl, pyridinylmethyl, amino, methylamino, dimethylamino, aminocarbonyl, methylaminocarbonyl, azetidinylcarbonyl and pyrrolidinylcarbonyl.

Particular substituents which may be attached to the moiety Z include methoxycarbonyl, methoxymethyl and methylsulphonylaminomethyl.

Where E, Q and W, which may be the same or different, represent straight or branched alkylene chains, these may be, for example, methylene, ethylene, 1-methylethylene, propylene, 2-methylpropylene or butylene. In addition, Q and W may be substituted in any position by a hydroxy group giving rise, for example, to a hydroxymethylmethylene, 2-hydroxypropylene or 2-hydroxymethylpropylene linkage. Moreover, Q may be substituted in any position by one or more fluorine atoms giving rise, for example, to a 2-fluoropropylene, 2,2-difluoropropylene or 2-fluoromethyl-propylene linkage. Furthermore, E and W may each independently represent a chemical bond. Where E represents a chemical bond, the moiety Z is attached directly to the central fused bicyclic heteroaromatic ring system containing the variables T, U and V. Similarly, where W represents a chemical bond, the substituent $R^1$ is attached directly to the azetidine, pyrrolidine or piperidine ring of which M is the residue.

Suitably, E represents a chemical bond or a methylene linkage.

Suitably, Q represents an ethylene or propylene linkage.

The compound of formula I in accordance with the present invention is suitably an indole, benzofuran or benzthiophene derivative of formula IC, an indazole derivative of formula ID, or a pyrrolo[2,3-c]pyridine derivative of formula IE:

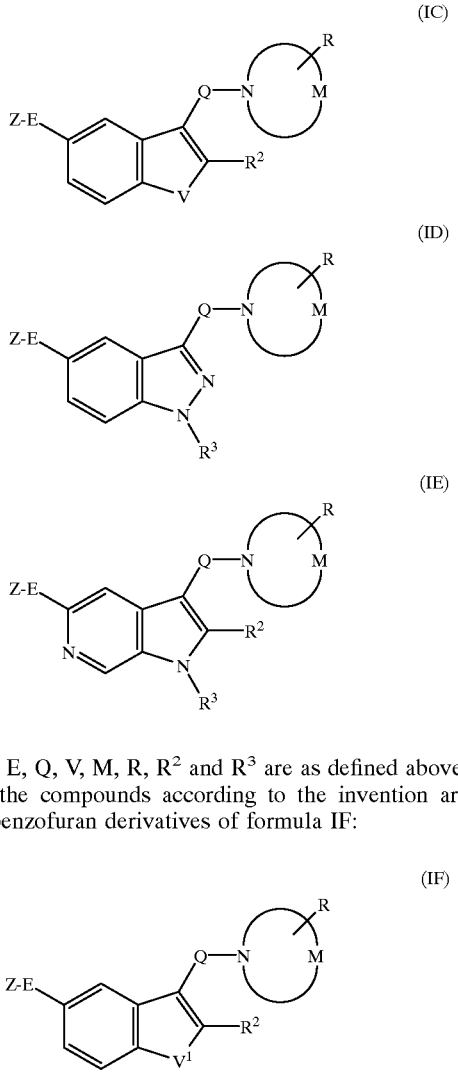

wherein Z, E, Q, V, M, R, $R^2$ and $R^3$ are as defined above. Typically, the compounds according to the invention are indole or benzofuran derivatives of formula IF:

wherein $V^1$ represents oxygen or N—$R^3$, and Z, E, Q, M, R, $R^2$ and $R^3$ are as defined above, in particular wherein $R^2$ and $R^3$ are both hydrogen.

Suitably, W represents a chemical bond or a methylene or hydroxymethyl-methylene linkage, in particular a chemical bond or a methylene linkage.

Suitably, $R^x$ and $R^y$ independently represent hydrogen, $C_{1-6}$ alkyl, $C_{2-6}$ alkenyl, $C_{3-7}$ cycloalkyl($C_{1-6}$)alkyl, indanyl, aryl, aryl($C_{1-6}$)alkyl, heteroaryl or heteroaryl($C_{1-6}$)alkyl, any of which groups may be optionally substituted by one or more substituents selected typically from $C_{1-6}$ alkyl, halogen, hydroxy, $C_{1-6}$ alkoxy, aminocarbonyloxy, amino, $C_{2-6}$ alkylcarbonylamino, $C_{1-6}$ alkylsulphonylamino and $C_{1-6}$ alkylaminosulphonylmethyl. Particular values of $R^x$ and $R^y$ include hydrogen, methyl, hydroxyethyl, isobutyl, 2,2-dimethylpropyl, allyl, dimethylallyl, 1-cyclohexylethyl, 2-cyclohexylethyl, indanyl, hydroxy-indanyl, phenyl, benzyl, methyl-benzyl, fluorobenzyl, methoxy-benzyl, acetylamino-benzyl, 1-phenylethyl, 2-phenylethyl, 2-hydroxy-1-phenylethyl, 2-methoxy-1-phenylethyl, 2-aminocarbonyloxy-1-phenylethyl, 1-(fluorophenyl)ethyl, 1-(fluorophenyl)-2-hydroxyethyl, 1-(fluorophenyl)-2-methoxyethyl, 1-(acetylamino-phenyl)ethyl, 2-(acetylamino-phenyl)ethyl, 2-hydroxy-1-phenylprop-1-yl, 1-phenylprop-2-yl, 2-phenylprop-2-yl, 1-hydroxy-1-phenylprop-2-yl, 1-hydroxy-2-phenylprop-2-yl, 1-hydroxy-3-phenylprop-2-yl, furylmethyl, thienylmethyl and pyridylmethyl.

Specific values of $R^x$ and $R^y$ include methyl, benzyl and 1-phenylethyl.

In addition, where $R^x$ and $R^y$ together represent an optionally substituted or phenyl ring-fused $C_{2-6}$ alkylene group, the substituent —$NR^xR^y$ as defined for $R^1$ may suitably represent 3,3-dimethylpiperidinyl, 2-phenylpiperidinyl, 3-hydroxy-2-phenylpiperidinyl or 1,2,3,4-tetrahydroisoquinolin-2-yl.

Suitable values for the substituent $R^1$ include hydroxy, benzyloxy, methoxy-benzyloxy, pyridylmethoxy, benzylthio, fluorobenzyl-thio, phenylsulphinyl, benzylsulphinyl, fluorobenzyl-sulphinyl, fluorobenzyl-sulphonyl, amino, methylamino, indanylamino, hydroxyindanyl-amino, benzylamino, N-(methylbenzyl)-amino, N-(acetylamino-benzyl)-amino, N-(1-phenylethyl)-amino, N-(2-phenylethyl)-amino, N-(2-hydroxy-1-phenylethyl)-amino, N-(2-methoxy-1-phenylethyl)-amino, N-(2-aminocarbonyloxy-1-phenylethyl)-amino, N-[1-(fluorophenyl)ethyl]-amino, N-[1-(fluorophenyl)-2-hydroxyethyl]-amino, N-[1-(fluorophenyl)-2-methoxyethyl]-amino, N-[1-(acetylamino-phenyl)ethyl]-amino, N-[2-(acetylamino-phenyl)ethyl]-amino, N-(2-hydroxy-1-phenylprop-1-yl)-amino, N-(1-phenylprop-2-yl)-amino, N-(2-phenylprop-2-yl)-amino, N-(1-hydroxy-1-phenylprop-2-yl)-amino, N-(1-hydroxy-2-phenylprop-2-yl)-amino, N-(1-hydroxy-3-phenylprop-2-yl)-amino, N-(furylmethyl)-amino, N-(pyridylmethyl)-amino, dimethylamino, N-isobutyl-N-methylamino, N-(2,2-dimethylpropyl)-N-methylamino, N-allyl-N-methylamino, N-(3,3-dimethylprop-2-en-1-yl)-N-methylamino, N-(1-cyclohexylethyl)-N-methylamino, N-benzyl-N-methylamino, N-methyl-N-(methylbenzyl)-amino, N-(fluorobenzyl)-N-methylamino, N-(acetylamino-benzyl)-N-methylamino, N-methyl-N-(1-phenylethyl)-amino, N-methyl-N-(2-phenylethyl)-amino, N-(2-hydroxy-1-phenylethyl)-N-methylamino, N-(2-methoxy-1-phenylethyl)-N-methylamino, N-[2-(acetylamino-phenyl)ethyl]-N-methylamino, N-(furylmethyl)-N-methylamino, N-methyl-N-(thienylmethyl)-amino, N-benzyl-N-(2-hydroxyethyl)-amino, N,N-bis(furylmethyl)-amino, 3,3-dimethylpiperidinyl, 2-phenylpiperidinyl, 3-hydroxy-2-phenylpiperidinyl and 1,2,3,4-tetrahydroisoquinolin-2-yl.

Specific values of $R^1$ include N-benzyl-N-methylamino and N-methyl-N-(1-phenylethyl)-amino.

Particular values of the group R include hydroxy, benzyloxy, benzyloxymethyl, methoxy-benzyloxy, pyridylmethoxy, benzylthio-methyl, fluorobenzylthio-methyl, phenylsulphinylmethyl, benzylsulphinylmethyl, fluorobenzyl-sulphinyl, fluorobenzyl-sulphinylmethyl, fluorobenzyl-sulphonylmethyl, indanylamino, indanylaminomethyl, hydroxyindanyl-amino, benzylamino, benzylaminomethyl, 1-(N-benzylamino)-2-hydroxyethyl, N-(methylbenzyl)-aminomethyl, N-(acetylamino-benzyl)-amino, N-(acetylamino-benzyl)-aminomethyl, N-(1-phenylethyl)-amino, N-(1-phenylethyl)-aminomethyl, N-(2-phenylethyl)-aminomethyl, N-(2-hydroxy-1-phenylethyl)-amino, N-(2-hydroxy-1-phenylethyl)-aminomethyl, N-(2-methoxy-1-phenylethyl)-amino, N-(2-aminocarbonyloxy-1-phenylethyl)-amino, N-[1-(fluorophenyl)ethyl]-amino, N-[1-(fluorophenyl)-2-hydroxyethyl]-amino, N-[1-(fluorophenyl)-2-methoxyethyl]-amino, N-[1-(acetylamino-phenyl)ethyl]-amino, N-[1-(acetylamino-phenyl)ethyl]-aminomethyl, N-[2-(acetylamino-phenyl)ethyl]-amino, N-(2-hydroxy-1-phenylprop-1-yl)-amino, N-(1-phenylprop-2-yl)-amino, N-(2-phenylprop-2-yl)-aminomethyl, N-(1-hydroxy-1-phenylprop-2-yl)-amino, N-(1-hydroxy-2-phenylprop-2-yl)-amino, N-(1-hydroxy-3-phenylprop-2-yl)-amino, N-(furylmethyl)-amino, N-(furylmethyl)-aminomethyl, N-(pyridylmethyl)-aminomethyl, N-isobutyl-N-methyl-aminomethyl, N-(2,2-dimethylpropyl)-N-methyl-aminomethyl, N-allyl-N-methylamino, N-(3,3-dimethylprop-2-en-1-yl)-N-methylamino, N-(1-cyclohexylethyl)-N-methyl-aminomethyl, N-benzyl-N-methylamino, N-benzyl-N-methyl-aminomethyl, N-methyl-N-(methylbenzyl)-aminomethyl, N-(fluorobenzyl)-N-methylamino, N-(acetylamino-benzyl)-N-methyl-aminomethyl, N-methyl-N-(1-phenylethyl)-aminomethyl, N-methyl-N-(2-phenylethyl)-aminomethyl, N-(2-hydroxy-1-phenylethyl)-N-methylamino, N-(2-hydroxy-1-phenylethyl)-N-methyl-aminomethyl, N-(2-methoxy-1-phenylethyl)-N-methylamino, N-[2-(acetylamino-phenyl)ethyl]-N-methylamino, N-(furylmethyl)-N-methylamino, N-methyl-N-(thienylmethyl)-amino, N-benzyl-N-(2-hydroxyethyl-aminomethyl, N,N-bis(furylmethyl)-amino, 3,3-dimethylpiperidinylmethyl, 2-phenylpiperidinyl, 2-phenylpiperidinylmethyl, 3-hydroxy-2-phenylpiperidinylmethyl and 1,2,3,4-tetrahydroisoquinolin-2-yl.

Specific values of R include N-benzyl-N-methylamino and N-methyl-N-(1-phenylethyl)-aminomethyl.

Suitably, $R^2$ and $R^3$ independently represent hydrogen or methyl, especially hydrogen.

A particular sub-class of compounds according to the invention is represented by the compounds of formula IIA, and salts and prodrugs thereof:

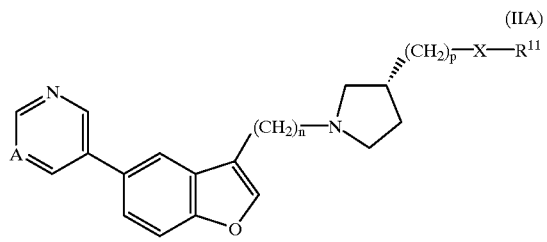

(IIA)

wherein
n is 2, 3 or 4;
p is zero, 1 or 2;
A represents nitrogen or C—$R^5$;
$R^5$ represents hydrogen, $C_{2-4}$ alkoxycarbonyl, $C_{1-3}$ alkoxy($C_{1-3}$)alkyl or $C_{1-3}$ alkylsulphonylamino($C_{1-3}$)alkyl;

X represents oxygen, sulphur, —SO—, —$SO_2$— or N—$R^{12}$; and
$R^{11}$ and $R^{12}$ independently represent hydrogen, $C_{1-6}$ alkyl, $C_{2-6}$ alkenyl, $C_{3-7}$ cycloalkyl($C_{1-6}$)alkyl, indanyl, aryl, aryl($C_{1-6}$)alkyl, heteroaryl or heteroaryl($C_{1-6}$) alkyl, any of which groups may be optionally substituted.

Examples of suitable optional substituents on the groups $R^{11}$ and $R^{12}$ include $C_{1-6}$ alkyl, halogen, cyano, trifluoromethyl, hydroxy, $C_{1-6}$ alkoxy, aminocarbonyloxy, $C_{2-6}$ alkylcarbonyl, amino, $C_{1-6}$ alkylamino, di($C_{1-6}$)alkylamino, $C_{2-6}$ alkylcarbonylamino, $C_{1-6}$ alkylsulphonylamino and $C_{1-6}$ alkylaminosulphonylmethyl.

Particular values of $R^5$ include hydrogen, methoxycarbonyl, methoxymethyl and methylsulphonylaminomethyl, especially hydrogen.

Suitably, X represents N—$R^2$.

Particular values of $R^{11}$ and $R^{12}$ include hydrogen, methyl, hydroxyethyl, isobutyl, 2,2-dimethylpropyl, allyl, dimethylallyl, 1-cyclohexylethyl, 2-cyclohexylethyl, indanyl, hydroxy-indanyl, phenyl, benzyl, methyl-benzyl, fluorobenzyl, methoxy-benzyl, acetylamino-benzyl, 1-phenylethyl, 2-phenylethyl, 2-hydroxy-1-phenylethyl, 2-methoxy-1-phenylethyl, 2-aminocarbonyloxy-1-phenylethyl, 1-(fluorophenyl)ethyl, 1-(fluorophenyl)-2-hydroxyethyl, 1-(fluorophenyl)-2-methoxyethyl, 1-(acetylamino-phenyl)ethyl, 2-(acetylamino-phenyl)ethyl, 2-hydroxy-1-phenylprop-1-yl, 1-phenylprop-2-yl, 2-phenylprop-2-yl, 1-hydroxy-1-phenylprop-2-yl, 1-hydroxy-2-phenylprop-2-yl, 1-hydroxy-3-phenylprop-2-yl, furylmethyl, thienylmethyl and pyridylmethyl.

Specific values of $R^{11}$ and $R^{12}$ include methyl, benzyl and 1-phenylethyl.

In relation to formula IIA, the variable n is preferably 2.
In relation to formula IIA, the variable p is preferably 1.
Another sub-class of compounds according to the invention is represented by the compounds of formula IIB, and salts and prodrugs thereof:

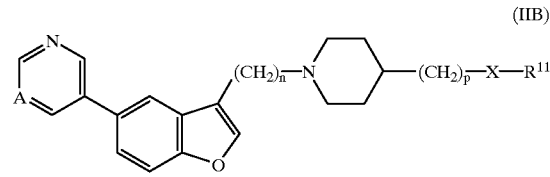

(IIB)

wherein n, p, A, X and $R^{11}$ are as defined with reference to formula IIA above.

In relation to formula IIB, the variable n is preferably 3.
In relation to formula IIB, the variable p is suitably zero or 1.

Specific compounds within the scope of the present invention include:
N-methyl-N-[(1S)-1-phenylethyl]-N-[(3R)-1-(2-(5-(pyridin-3-yl)benzofuran-3-yl)ethyl)pyrrolidin-3-ylmethyl]amine;
4-(N-benzyl-N-methyl)amino-1-[3-(5-(pyridin-3-yl)benzofuran-3-yl)propyl]piperidine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention wherein T represents CH, U represents C—$R^2$ and V represents N—$R^3$, corresponding to the indole derivatives of formula IF as defined above wherein $V^1$ represents N—$R^3$, may be prepared by a process which comprises reacting a compound of formula III:

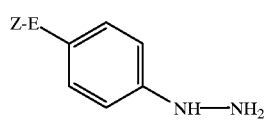

(III)

wherein Z and E are as defined above; with a compound of formula IV, or a carbonyl-protected form thereof:

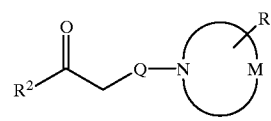

(IV)

wherein $R^2$, Q, M and R are as defined above; followed, where required, by N-alkylation by standard methods to introduce the moiety $R^3$.

The reaction between compounds III and IV, which is an example of the well-known Fischer indole synthesis, is suitably carried out by heating the reagents together under mildly acidic conditions, e.g. 4% sulphuric acid at reflux.

Suitable carbonyl-protected forms of the compounds of formula IV include the dimethyl acetal or ketal derivatives. Where the alkylene chain Q is substituted by a hydroxy group, this group may condense with the carbonyl moiety in compound IV whereby the carbonyl moiety is protected in the form of a cyclic hemiacetal.

The Fischer reaction between compounds III and IV may be carried out in a single step, or may proceed via an initial non-cyclising step at a lower temperature to give an intermediate of formula V:

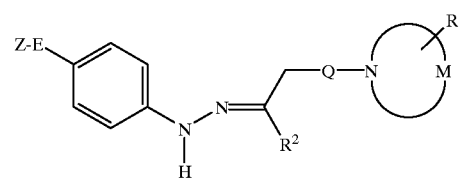

(V)

wherein Z, E, Q, $R^2$, M and R are as defined above; followed by cyclisation using a suitable reagent, e.g. a polyphosphate ester.

The intermediates of formula IV, or carbonyl-protected forms thereof, may be prepared by reacting a compound of formula VI, or a carbonyl-protected form thereof, with a compound of formula VII:

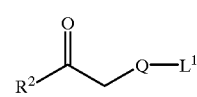

(VI)

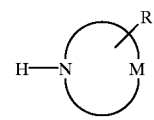

(VII)

wherein Q, $R^2$, M and R are as defined above, and $L^1$ represents a suitable leaving group.

The leaving group $L^1$ is suitably a halogen atom, e.g. chlorine or bromine.

Where $L^1$ represents a halogen atom, the reaction between compounds VI and VII is conveniently effected by stirring the reactants under basic conditions in a suitable solvent, for example sodium carbonate or potassium carbonate in 1,2-dimethoxyethane or N,N-dimethyl-formamide, or triethylamine in tetrahydrofuran or acetonitrile, optionally in the presence of catalytic sodium iodide.

In an alternative procedure, the compounds according to the invention may be prepared by a process which comprises reacting a compound of formula VII as defined above with a compound of formula VIII:

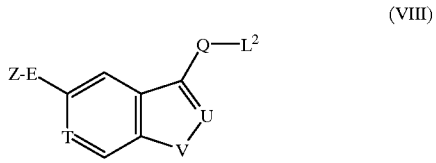

(VIII)

wherein Z, E, Q, T, U and V are as defined above, and $L^2$ represents a suitable leaving group.

The leaving group $L^2$ is suitably an alkylsulphonyloxy or arylsulphonyloxy group, e.g. methanesulphonyloxy (mesyloxy) or p-toluenesulphonyloxy (tosyloxy).

Where $L^2$ represents an alkylsulphonyloxy or arylsulphonyloxy group, the reaction between compounds VII and VIII is conveniently carried out in a suitable solvent such as isopropanol or 1,2-dimethoxy-ethane, typically in the presence of a base such as sodium carbonate or potassium carbonate, optionally in the presence of sodium iodide.

In one representative approach, the compounds of formula VIII wherein T and U both represent CH, V represents NH and $L^2$ represents a mesyloxy or tosyloxy group may be prepared by the sequence of steps illustrated in the following reaction scheme (cf. Larock and Yum, *J. Am. Chem. Soc.*, 1991, 113, 6689):

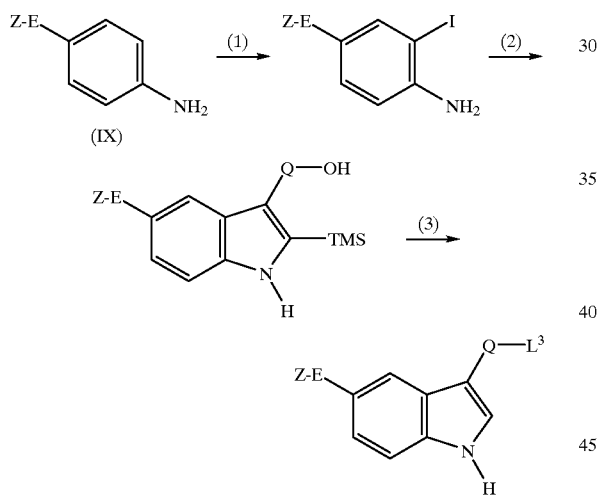

wherein Z, E and Q are as defined above, $L^3$ represents mesyloxy or tosyloxy, and TMS is an abbreviation for trimethylsilyl.

In Step 1 of the reaction scheme, the aniline derivative IX is treated with iodine monochloride, advantageously in methanol in the presence of a base such as calcium carbonate, in order to introduce an iodine atom ortho to the amine moiety. Step 2 involves a palladium-mediated coupling reaction with the protected acetylene derivative TMS—C≡C—Q—OH, typically using palladium acetate and triphenylphosphine in the presence of lithium chloride and sodium carbonate, suitably in N,N-dimethyl-formamide at an elevated temperature. This is followed in Step 3 by removal of the TMS moiety, ideally in refluxing methanolic hydrochloric acid; followed in turn by mesylation or tosylation, suitably by using mesyl chloride or tosyl chloride respectively in pyridine.

In another representative approach, the compounds of formula VIII wherein T and U both represent CH, V represents NH, Q represents a propylene chain and $L^2$ represents a mesyloxy or tosyloxy group may be prepared by reacting 3,4-dihydro-2H-pyran with a compound of formula III as defined above or a salt thereof, under a variant of the Fischer reaction conditions as described above for the reaction between compounds III and IV; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by heating the hydrazine derivative III or an acid addition salt thereof, typically the hydrochloride salt, in an inert solvent such as dioxan, advantageously in the presence of a mineral acid such as hydrochloric acid or a Lewis acid such as zinc chloride, at the reflux temperature of the solvent.

In another procedure, the compounds according to the invention wherein E represents a chemical bond may be prepared by reacting a compound of formula X with a compound of formula XI:

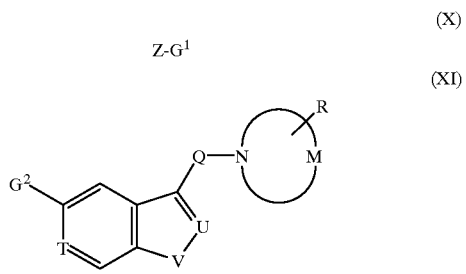

wherein Z, Q, T, U, V, M and R are as defined above; one of $G^1$ and $G^2$ represents a suitable leaving group, and the other represents a boronic acid moiety —B(OH)$_2$ or a $C_{1-4}$ alkyl ester or anhydride thereof; in the presence of a transition metal catalyst.

The leaving group $G^1$ or $G^2$ is suitably a halogen atom, e.g. bromine.

The transition metal catalyst of use in the reaction between compounds X and XI is suitably tetrakis (triphenylphosphine)palladium (0). The reaction is conveniently carried out in an inert solvent such as aqueous 1,2-dimethoxyethane, advantageously in the presence of a base such as sodium acetate or sodium carbonate, typically at an elevated temperature.

In a further procedure, the compounds according to the invention wherein T represents CH, U represents nitrogen and V represents N—$R^3$, corresponding to the indazole derivatives of formula ID as defined above, may be prepared by a process which comprises cyclising a compound of formula XII:

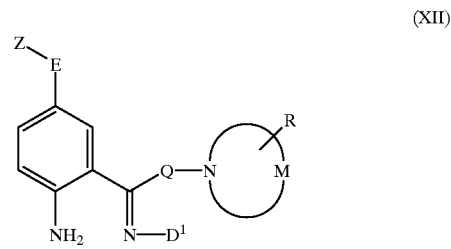

wherein Z, E, Q, M and R are as defined above, and $D^1$ represents a readily displaceable group; followed, where required, by N-alkylation by standard methods to introduce the moiety $R^3$.

The cyclisation of compound XII is conveniently achieved in a suitable organic solvent at an elevated temperature, for example in a mixture of m-xylene and 2,6-lutidine at a temperature in the region of 140° C.

The readily displaceable group $D^1$ in the compounds of formula XII suitably represents a $C_{1-4}$ alkanoyloxy group, preferably acetoxy. Where $D^1$ represents acetoxy, the desired compound of formula XII may be conveniently prepared by treating a carbonyl compound of formula XIII:

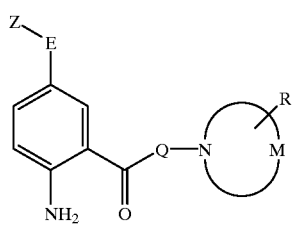

(XIII)

wherein Z, E, Q, M and R are as defined above; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XIII may conveniently be prepared by ozonolysis of the corresponding indole derivative of formula XIV:

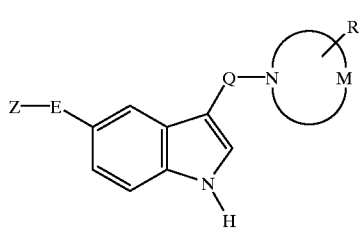

(XIV)

wherein Z, E, Q, M and R are as defined above; followed by a reductive work-up, advantageously using dimethylsulphide.

The indole derivatives of formula XIV may be prepared by methods analogous to those described in the accompanying Examples, or by procedures well known from the art.

In a still further procedure, the compounds according to the invention wherein T represents CH, U represents C—$R^2$ and V represents oxygen or sulphur, corresponding to the benzofuran or benzthiophene derivatives of formula IC wherein V is oxygen or sulphur respectively, may be prepared by a process which comprises cyclising a compound of formula XV:

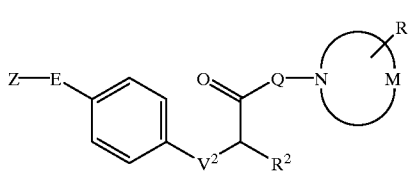

(XV)

wherein Z, E, Q, $R^2$, M and R are as defined above, and $V^2$ represents oxygen or sulphur.

The cyclisation of compound XV is conveniently effected by using polyphosphoric acid or a polyphosphate ester, advantageously at an elevated temperature.

The compounds of formula XV may be prepared by reacting a compound of formula XVI with a compound of formula XVII:

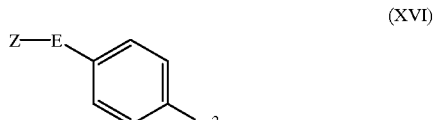

(XVI)

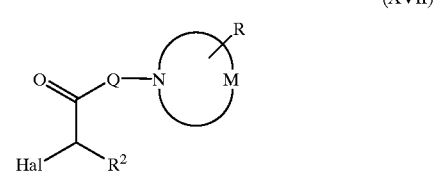

(XVII)

wherein Z, E, Q, $R^2$, $V^2$, M and R are as defined above, and Hal represents a halogen atom.

The reaction is conveniently effected in the presence of a base such as sodium hydroxide.

In a yet further procedure, the compounds according to the invention may be prepared by a process which comprises reducing a compound of formula XVIII:

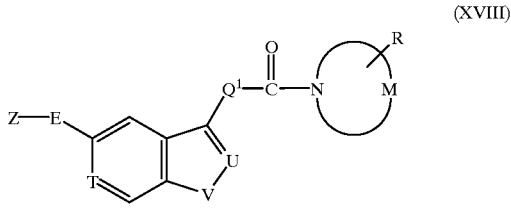

(XVIII)

wherein Z, E, T, U, V, M and R are as defined above, and —$Q^1$—$CH_2$— corresponds to the moiety Q as defined above.

The reaction is suitably carried out by treating the compound of formula XVIII with a reducing agent such as lithium aluminium hydride in an appropriate solvent, e.g. diethyl ether, tetrahydrofuran or mixtures thereof.

The compounds of formula XVIII above may suitably be prepared by reacting a compound of formula VII as defined above with the appropriate compound of formula XIX:

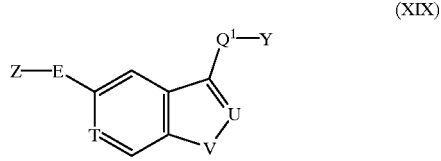

(XIX)

wherein Z, E, T, U, V and $Q^1$ are as defined above, and Y represents a reactive carboxylate moiety.

Suitable values for the reactive carboxylate moiety Y include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula XIX above wherein Y is an acid chloride moiety may be prepared by treating the corresponding carboxylic acid derivative with thionyl chloride in toluene. Similarly, the intermediates of formula XIX wherein Y is an acylimidazole moiety may be prepared by treating the corresponding carboxylic acid derivative with 1,1'-carbonyldiimidazole. Alternatively, the reactive carboxylate moiety Y may be obtained by treating the corresponding compound wherein Y is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula VII.

In one additional procedure, the compounds according to the invention may be prepared by a process which comprises reacting a compound of formula VII as defined above with a compound of formula XX:

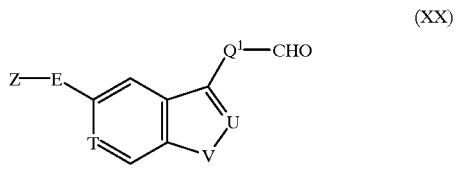

(XX)

wherein Z, E, T, U, V and $Q^1$ are as defined above; in the presence of a reducing agent.

Similarly, the compounds of formula XI above may be prepared by reacting a compound of formula VII as defined above with a compound of formula XXI:

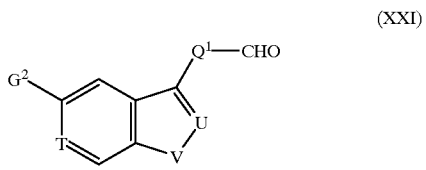

(XXI)

wherein T, U, V, $G^2$ and $Q^1$ are as defined above; in the presence of a reducing agent.

A suitable reducing agent for use in conjunction with the above reaction between compound VII and compound XX or XXI is sodium triacetoxyborohydride, in which case the reaction is conveniently effected in the presence of acetic acid and a solvent such as dichloromethane.

The compounds of formula XX and XXI may be prepared by reduction of the appropriate compound of formula XXII:

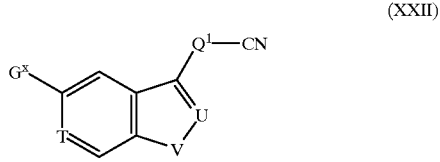

(XXII)

wherein T, U, V and $Q^1$ are as defined above; and $G^x$ corresponds to the moiety Z—E— as defined above, or $G^x$ corresponds to the group of formula $G^2$ as defined above.

A suitable reducing agent for effecting the transformation of the cyano moiety in compound XXII to the carboxaldehyde (CHO) moiety in compounds XX and XXI is diusobutylaluminium hydride (DIBAL—H), and the reaction is conveniently carried out in a solvent such as dichloromethane.

A representative approach to the nitrile intermediates of formula XXII in which T and U both represent CH, V is oxygen and $Q^1$ is an ethylene linkage can be illustrated as follows:

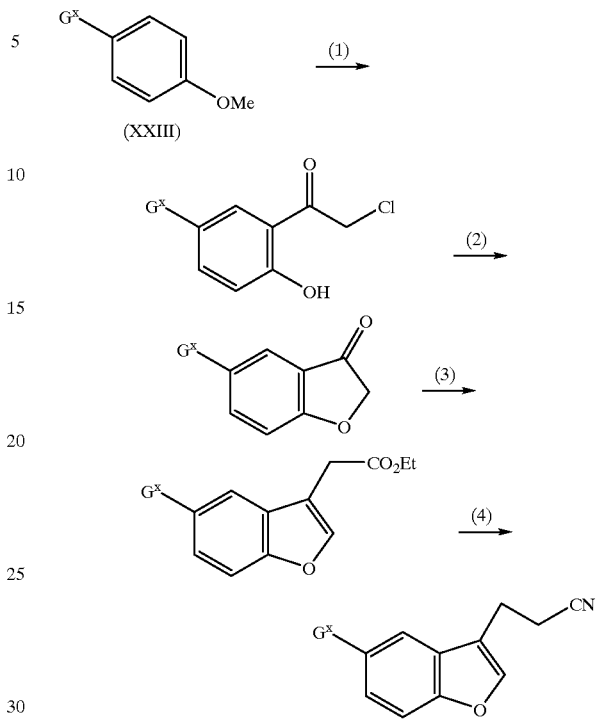

in which $G^x$ is as defined above.

In Step 1, the anisole derivative XXIII is treated with chloroacetyl chloride in the presence of aluminium chloride, whereby the methoxy substituent is demethylated, with concomitant introduction of the chloroacetyl moiety ortho to the resulting phenolic OH. This compound is then cyclised in Step 2, by treatment with methanolic sodium acetate at an elevated temperature. Step 3 comprises treatment of the resulting furanone derivative with triethyl phosphonoacetate in the presence of a strong base such as potassium hexamethyldisilazide, followed in Step 4 by DIBAL—H reduction of the ethyl ester moiety in the resulting compound. The hydroxyethyl benzofuran derivative thereby obtained is mesylated, and the mesyl group thereof subsequently displaced by cyanide ion, to afford the desired cyanoethyl benzofuran analogue.

The intermediates of formula XI above may suitably be prepared by reacting a compound of formula VII as defined above with a compound of formula XXIV:

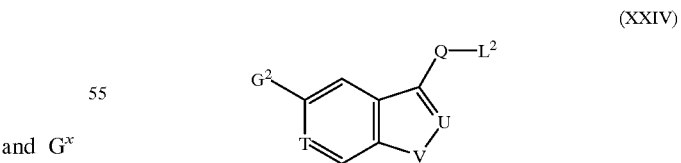

(XXIV)

wherein Q, T, U, V, $L^2$ and $G^2$ are as defined above; under conditions analogous to those described above for the reaction between compounds VII and VIII.

Typical intermediates of formula XXIV, wherein T and U are both CH, V is oxygen, Q is an ethylene linkage and $L^2$ is mesyl or tosyl, can be prepared from compound XXIII, in which $G^x$ corresponds to the group $G^2$, by following Steps 1 to 3 of the reaction scheme illustrated immediately above to obtain the ethyl ester intermediate, which can then be reduced with DIBAL—H and mesylated or tosylated under standard conditions.

Where they are not commercially available, the starting materials of formula III, VI, VII, IX, X, XVI, XVII, XIX and XXIII may be prepared by the methods described in the accompanying Examples, or by analogous procedures which will be apparent to those skilled in the art.

It will be understood that any compound of formula I initially obtained from any of the above processes may, where appropriate, subsequently be elaborated into a further compound of formula I by techniques known from the art. For example, a compound of formula I wherein $R^x$ is benzyl initially obtained may be converted into a compound of formula I wherein $R^x$ is hydrogen typically by conventional catalytic hydrogenation, or by transfer hydrogenation using a hydrogenation catalyst such as palladium on charcoal in the presence of a hydrogen donor such as ammonium formate. Moreover, a compound of formula I wherein $R^1$ is hydroxy initially obtained may be converted into the corresponding carbonyl compound (aldehyde or ketone) by treatment with a conventional oxidising agent such as sulphur trioxide-pyridine complex; the resulting carbonyl compound may then be converted in turn into a compound of formula I wherein $R^1$ represents —$NHR^y$, suitably by a standard reductive amination procedure which comprises treating the carbonyl compound with the appropriate amine of formula $R^y$—$NH_2$ in the presence of a suitable reducing agent, typically sodium cyanoborohydride. Furthermore, a compound of formula I wherein $R^1$ represents —$NHR^y$ initially obtained may be converted into a further compound of formula I wherein $R^1$ represents —$NR^xR^y$, in which $R^x$ corresponds to the group —$CH_2R^z$, suitably by a reductive amination procedure which comprises treating the compound of formula I wherein $R^1$ represents —$NHR^y$ with the appropriate aldehyde of formula $R^z$—CHO in the presence of a reducing agent such as sodium cyanoborohydride. In addition, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-$HT_{1D\alpha}$ receptor subtype, inhibit forskolin-stimulated adenylyl cyclase activity, and stimulate [$^{35}$S]-GTPγS binding to membranes from clonal cell lines expressing human cloned receptors.

5-$HT_{1D\alpha}$/5-$HT_{1D\beta}$ Radioligand Binding

Chinese hamster ovary (CHO) clonal cell lines expressing the human 5-$HT_{1D\alpha}$ and 5-$HT_{1D\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, $CaCl_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the 5-$HT_{1D\alpha}$ receptor subtype obtained for the compounds of the accompanying Examples were below 50 nM in each case. Furthermore, the compounds of the accompanying Examples were all found to possess a selective affinity for the 5-$HT_{1D\alpha}$ receptor subtype of at least 10-fold relative to the 5-$HT_{1D\beta}$ subtype.

5-$HT_{1D\alpha}$/5-$HT_{1D\beta}$ Adenylyl Cyclase Assay

Studies were performed essentially as described in *J. Pharinacol. Exp. Ther.*, 1986, 238, 248. CHO clonal cell lines expressing the human cloned 5-$HT_{1D\alpha}$ and 5-$HT_{1D\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was incubated, for 10–15 min, in a final volume of 50 μl, at 30° C., with or without forskolin (10 μM), in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM $MgCl_2$, 1 mM EGTA, 1 mM 3-isobutyl- 1-methylxanthine, 3.5 mM creatinine phosphate, 0.2 mg/ml creatine phosphokinase, 0.5–1 μCi α-[$^{33}$P]-ATP and 1 nCi [$^{3}$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic ALMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-HT$_{1D\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D\alpha}$ receptor subtype relative to the 5-HT$_{1D\beta}$ subtype.

5-HT$_{1D\alpha}$/5-HT$_{1D\beta}$ GTP$_{\gamma}$S Binding

Studies were performed essentially as described in *Br. J. Pharmacol.*, 1993, 109, 1120. CHO clonal cell lines expressing the human cloned 5-HT$_{1D\alpha}$ and 5-HT$_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, MgCl$_2$ 10, pargyline 0.01; ascorbate 0.1%; pH 7.4 at room temperature) at a concentration of 40 μg protein/ml for the 5-HT$_{1D\alpha}$ receptor transfected cells and 40–50 μg protein/ml for the 5-HT$_{1D\beta}$ receptor transfected cells. The membrane suspension was then incubated, in a volume of 1 ml, with GDP (100 μM for 5-HT$_{1D\alpha}$ receptor transfected cells, 30 μM for the 5-HT$_{1D\beta}$ receptor transfected cells) and test compound at 30° C. for 20 min and then transferred to ice for a further 15 min. [$^{35}$S]-GTP$_{\gamma}$S was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-HT$_{1D\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D\alpha}$ receptor subtype relative to the 5-HT$_{1D\beta}$ subtype.

EXAMPLE 1

N-Methyl-N-[(1S)-1-phenylethyl]-N-[(3R)-1-(2-(5-(pyridin-3-yl)benzofuran-3-yl)ethyl)pyrrolidin-3-ylmethyl]amine 3 hydrogen oxalate Step 1: 1-(5-Bromo-2-hydroxyphenyl)-2-chloroethanone To a solution of 4-bromoanisole (17.4 ml, 138 mmol) in dichloromethane (150 ml) was added chloroacetyl chloride (32 ml, 400 mmol) followed by aluminium chloride (60 g, 450 mmol) keeping the temperature below 30° C. The yellow solution was heated to reflux for 8 hours, cooled down to ambient temperature, then ice water was added very carefully. The organic layer was separated and the aqueous extracted once with dichloromethane. The combined organics were dried (sodium sulphate) then evaporated to give an oil which was purified by crystallisation from hexane. The title compound was obtained as a yellow solid (18 g, 52%). mp 80–82° C. $^1$H NMR (250 MHz, CDCl$_3$) δ 4.69 (2H, s), 6.95 (1H, d, J=9 Hz), 7.60 (1H, dd, J=1 and 9 Hz), 7.80 (1H, d, J=2 Hz), 11.59 (1H, s).

Step 2: 5-Bromobenzofuran-3-one

To a solution of the foregoing ethanone (18 g, 72 mmol) in methanol (150 ml) was added sodium acetate (7 g, 85 mmol). The solution was heated at 65° C. for 1 hour, then the methanol was evaporated. The residue was partitioned between dichloromethane and water. The organic layer was separated and the aqueous solution reextracted once with dichloromethane. The combined organics were dried (sodium sulphate) then evaporated to give a gum which was purified by column chromatography on alumina using dichloromethane to afford a solid (5.6 g, 36%). mp 102–106° C. $^1$H NMR (250 MHz, CDCl$_3$) δ 4.67 (2H, s), 7.05 (1H, d, J=9 Hz), 7.69 (1H, dd, J=2 and 9 Hz), 7.79 (H, d, J=2 Hz).

Step 3: 5-Bromobenzofuran-3-ylacetic acid ethyl ester

To a solution of triethyl phosphonoacetate (6 ml, 30.2 mmol) in dry tetrahydrofuran (200 ml) at −78° C. was added a solution of potassium bis(trimethylsilyl)amide in toluene (58 ml of a 0.5M solution). After stirring for 2 hours at −78° C., 5-bromobenzofuran-3-one (5.5 g, 26 mmol) was added dropwise. The resulting solution was stirred 1 hour at −78° C. and overnight at room temperature. Saturated aqueous ammonium chloride solution and ethyl acetate were added. The organic layer was separated and evaporated to dryness to give the crude title compound which was purified by column chromatography on silica using dichloromethane, followed by column chromatography on alumina using dichloromethane. 5-Bromobenzofuran-3-ylacetic acid ethyl ester was obtained as a low melting solid (4.2 g, 57%). mp 38–40° C. $^1$H NMR (250 MHz, CDCl$_3$) δ 1.28 (3H, t, J=7 Hz), 3.65 (2H, d, J=1 Hz), 4.20 (2H, q, J=7 Hz), 7.36 (1H, s), 7.38 (1H, d, J=2 Hz), 7.63 (1H, s), 7.71 (1H, d, J=2 Hz).

Step 4: 2-(5-Bromobenzofuran-3-yl)ethanol

To a solution of the foregoing ester (2.2 g, 7.8 mmol) in toluene (150 ml) under nitrogen at 5° C. was added diisobutylaluminium hydride in toluene (20 ml of a 1M solution). The solution was stirred 1 hour at 5° C. and 1 hour at ambient temperature, then methanol was added slowly followed by 10% aqueous potassium carbonate solution. The organic layer was decanted and the aqueous reextracted with ethyl acetate. The combined organics were filtered and evaporated to dryness to give the title compound (1.8 g, 96%) as an oil. $^1$H NMR (360 MHz, d$_6$-DMSO) δ 2.78 (2H, dt, J=1 and 7 Hz), 3.68 (2H, dt, J=5 and 7 Hz), 4.73 (1H, t, J=5 Hz), 7.43 (1H, dd, J=2 and 9 Hz), 7.53 (1H, d, J=9 Hz), 7.84 (1H, s), 7.88 (1H, d, J=2 Hz).

Step 5: N-Methyl-N-[(3R)-1-(2-(5-bromobenzofuran-3-yl)ethyl)pyrrolidin-3-ylmethyl]-N-[(1S)-1-phenylethyl]amine To a solution of 2-(5-bromobenzofuran-3-yl)ethanol (200 mg, 0.95 mmol) in dichloromethane (10 ml) at −5° C. under nitrogen was added triethylamine (0.21 ml, 1.5 mmol) followed by methanesulphonyl chloride (0.11 ml, 1.4 mmol). The solution was stirred for 20 minutes at −5° C., then washed twice with water, dried (sodium sulphate) and evaporated to give the mesylate which was redissolved in tetrahydrofuran (20 ml). N-Methyl-N-(1(S)-1-phenylethyl)-

N-(pyrrolidin-3(R)-ylmethyl)amine (220 mg, 1 mmol) (WO 96/04274) was added followed by potassium carbonate (138 mg, 1 mmol) and the solution was heated to reflux for 24 hours. The solvent was evaporated and the residue partitioned between dichloromethane and water. The organic layer was separated, dried (sodium sulphate), evaporated and the oil purified by column chromatography on silica using a methanol/dichloromethane gradient to give the title compound (110 mg, 24%) as an oil. $^1$H NMR (250 MHz, CDCl$_3$) δ 1.35 (3H, d, J=7 Hz), 1.40–1.57 (1H, m), 1.88–2.10 (1H, m), 2.19 (3H, s), 2.22–2.64 (5H, m), 2.66–2.94 (6H, m), 3.62 (1H, q, J=7 Hz), 7.18–7.42 (7H, m), 7.45 (1H, s), 7.68 (1H, d, J=2 Hz). MS, m/z=441 and 443 for (M+H)$^+$.

Step 6: N-Methyl-N-[(1S)-1-phenylethyl]-N-[(3R)-1-(2-(5-(pyridin-3-yl)benzofuran-3-yl)ethyl)pyrrolidin-3-ylmethyl]amine 3 hydrogen oxalate To a solution of the foregoing 5-bromobenzofuran (100 mg, 0.23 mmol) in ethylene glycol dimethyl ether (10 ml) was added 3-pyridyl boronic acid (36 mg, 0.3 mmol) (Tarashima M. et al., Japan. Chem. Phar. Bull. 1983, 31(12), 4573), sodium acetate (65 mg, 0.61 mmol) and water (5 ml). The solution was purged with nitrogen for 2 hours. Tetrakis (triphenylphosphine)palladium (0) (200 mg) was added and the mixture stirred for 2 hours at reflux. After cooling down to ambient temperature, 10% aqueous sodium carbonate was added and the mixture extracted twice with ethyl acetate. The combined organics were washed with brine, dried (sodium sulphate) and evaporated. The residue was purified by column chromatography on silica using a methanol/dichloromethane gradient. The title compound was obtained as an oil (78 mg, 77%). The hydrogen oxalate had mp 75° C. (decomposition). $^1$H NMR (360 MHz, d$_6$-DMSO) δ 1.43 (3H, d, J=7 Hz), 1.60–1.74 (1H, m), 2.08–2.23 (1H, m), 2.29 (3H, s), 2.56–2.75 (3H, m), 3.00–3.10 (1H, m), 3.13 (2H, t, J=7 Hz), 3.27–3.60 (3H, m), 3.46 (2H, t, J=7 Hz), 3.97 (1H, q, J=7 Hz), 7.27–7.46 (5H, m), 7.51 (1H, dd, J=5 and 8 Hz), 7.71 (2H, s), 7.97 (1H, s), 8.09 (1H, s), 8.15 (1H, dd, J=2 and 8 Hz), 8.59 (1H, dd, J=2 and 5 Hz), 8.98 (1H, d, J=2 Hz). MS, m/z=440 for (M+H)$^+$. (Found: C, 55.59; H, 6.15; N, 5.74. C$_{29}$H$_{33}$N$_3$O. 3(CO$_2$H)$_2$. 2.5H$_2$O requires C, 55.70; H, 5.88; N, 5.57%).

EXAMPLE 2

4-(N-Benzyl-N-methylamino)-1-[3-(5-(pyridin-3-yl) benzofuran-3-yl)pronyl]-piperidine 3 hydrogen oxalate Step 1: 1-tert-Butyloxycarbonyl-4-(N-benzyl-N-methylamino)piperidine To a stirred solution of 1-tert-butyloxycarbonyl-4-piperidone (3.30 g, 16.5 mmol) and benzylamine (1.64 ml, 15.0 mmol) in a mixture of methanol (150 ml) and glacial acetic acid (3.4 ml, 60 mmol) was added sodium cyanoborohydride (1.04 g, 16.5 mmol), and the resulting mixture was stirred at room temperature for 2 hours 15 minutes. A solution of formaldehyde (38% w/v aqueous solution; 1.42 ml) in methanol (5 ml) was added and stirring was continued for 16 hours. 4N Sodium hydroxide (35 ml) was added and the methanol was removed under vacuum. The residue was diluted with water (50 ml) and products were extracted with diethyl ether (2×300 ml). The combined organic phases were washed with brine (50 ml), dried (Na$_2$SO$_4$) and concentrated. Flash chromatography of the residue (silica gel, dichloromethane-methanol-ammonia, 97:3:0.2) followed by repurification of impure fractions on alumina (activity III, dichloromethane) afforded 3.98 g (87.4%) of the title compound as a colourless thick oil; δ$_H$ (360 MHz, CDCl$_3$) 1.46 (9H, s), 1.44–1.56 (2H, m), 1.76–1.85 (2H, m), 2.20 (3H, s), 2.52–2.76 (3H, m), 3.57 (2H, s), 4.10–4.22 (2H, m), 7.20–7.36 (5H, m); m/e (ES) 305 (M$^+$+1).

Step 2: 4-(N-Benzyl-N-methylamino)piperidine

A solution of the preceding piperidine (3.95 g, 12.97 mmol) in a mixture of dichloromethane (40 ml) and trifluoroacetic acid (40 ml) was allowed to stand at room temperature for 3 hours. Solvents were removed under vacuum and the residue azeotroped with toluene-methanol (5:1, 100 ml). The remaining residue was dissolved in 4N sodium hydroxide (50 ml) and extracted with dichloromethane (2×150 ml). The combined organic solutions were washed with brine (50 ml), dried (Na$_2$SO$_4$) and concentrated to give the title compound (2.70 g, 100%) which was used in the next step without further purification; δ$_H$ (360 MHz, CDCl$_3$) 1.52 (2H, dq, J=12.2 and 4.0 Hz), 1.80–1.90 (2H, m), 2.21 (3H, s), 2.50–2.66 (3H, m), 3.12–3.22 (2H, m), 3.58 (2H, s), 7.18–7.36 (5H, m); m/e (ES) 205 (M$^+$+1).

Step 3: 4-(N-Benzyl-N-methylamino)-1-[3-(5-bromobenzofuran-3-yl)propyl]piperidine The title compound was obtained following the procedure described in Example 1 Step 5 using the amine from Example 2 Step 2. $^1$H NMR (250 MHz, CDCl$_3$) δ 1.72–2.00 (6H, m), 2.20 (3H, s), 2.32–2.46 (2H, m), 2.54–2.72 (3H, m), 2.92–3.06 (4H, m), 3.57 (2H, s), 7.20–7.42 (7H, m), 7.69 (1H, s), 7.70 (1H, s). MS, m/z=441 and 443 for (M+H)$^+$.

Step 4: 4-(N-Benzyl-N-methylamino)-1-[3-(5-(pyridin-3-yl)benzofuran-3-yl)propyl]piperidine 3 hydrogen oxalate The title compound was obtained following the procedure described in Example 1 Step 6 using the 5-bromobenzofuran from Example 2 Step 3. The hydrogen oxalate salt had mp>192° C. $^1$H NMR (360 MHz, d$_6$-DMSO) δ 1.88–2.03 (2H, m), 2.03–2.17 (4H, m), 2.33 (3H, s), 2.71–2.83 (2H, m), 2.83–2.97 (2H, m), 2.97–3.12 (3H, m), 3.43–3.58 (2H, m), 3.92 (2H, s), 7.26–7.46 (5H, m), 7.46–7.56 (1H, m), 7.60–7.70 (2H, m), 7.90 (1H, s), 8.01 (1H, s), 8.09–8.17 (1H, m), 8.57 (1H, dd, J=2 Hz and 5 Hz), 8.96 (1H, d, J=2 Hz). MS, m/z=440 for (M+H)$^+$. (Found: C, 59.06; H, 5.77; N, 5.73. C$_{29}$H$_{33}$N$_3$O 3(CO$_2$H)$_2$ requires C, 59.23; H, 5.54; N, 5.92%).

What is claimed is:

1. A compound of formula I, or a pharmaceutically acceptable salt thereof:

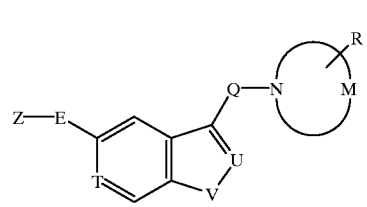

(I)

wherein

Z represents pyridine optionally substituted with one or more substituents independently selected from $C_{1-6}$ alkyl, $C_{2-6}$ alkenyl, $C_{2-6}$ alkynyl, $C_{3-7}$ cycloalkyl, aryl, aryl($C_{1-6}$)alkyl, halogen, halo($C_{1-6}$)alkyl, cyano, cyano ($C_{1-6}$)alkyl, trifluoromethyl, and —(CH$_2$)$_a$—R$^4$, in which a is zero, 1, 2 or 3 and R$^4$ represents —OR$^a$, —OCOR$^c$, —OCO$_2$R$^a$, —SR$^a$, —SOR$^a$, —SO$_2$R$^c$, —CH=CHSO$_2$R$^c$, —SO$_2$NR$^a$R$^b$, —CH=CHSO$_2$NR$^a$R$^b$, —NR$^a$R$^b$, —NR$^a$COR$^c$, —NR$^a$CO(CH$_2$)$_b$OR$^d$, in which b is 1 or 2, —NR$^a$CO$_2$R$^d$, —NR$^a$SO$_2$R$^c$, —NR$^d$CONR$^a$R$^b$, —NR$^d$SO$_2$NR$^a$R$^b$, —COR$^c$, —CH=CHCOR$^c$, —CO$_2$R$^a$, —CONR$^a$R$^b$, —CH=CHCONR$^a$R$^b$, and —CONR$^d$NR$^a$R$^b$, wherein R$^a$, R$^b$, R$^c$, and R$^d$ each independently represents hydrogen, C$_{1-6}$ alkyl, trifluoromethyl, phenyl, or fluorophenyl;

E represents a chemical bond or a straight or branched alkylene chain containing from 1 to 4 carbon atoms;

Q represents a straight or branched alkylene chain containing from 1 to 4 carbon atoms, optionally substituted in any position by one or more substituents selected from fluoro and hydroxy;

T represents CH;

U represents C—R$^2$;

V represents oxygen;

R$^2$ and R$^3$ independently represent hydrogen or C$_{1-6}$ alkyl;

M represents the residue of a pyrrolidine ring;

R represents a group of formula —W—R$^1$;

W represents a chemical bond or a straight or branched alkylene chain containing from 1 to 4 carbon atoms, optionally substituted in any position by a hydroxy group;

R$^1$ represents —OR$^x$, —SR$^x$, —SOR$^x$, —SO$_2$R$^x$ or —NR$^x$R$^y$;

R$^x$ and R$^y$ independently represent hydrogen or hydrocarbon, wherein said hydrocarbon is selected from the group consisting of C$_{1-6}$ alkyl, C$_{2-6}$ alkenyl, C$_{2-6}$ alkynyl, C$_{3-7}$ cycloalkyl, C$_{3-7}$cycloalkyl(C$_{1-6}$)alkyl, indanyl, aryl and aryl(C$_{1-6}$)alkyl, and said hydrocarbon is optionally substituted with one or more groups selected from C$_{1-6}$ alkyl, adamantyl, phenyl, halogen, C$_{1-6}$ haloalkyl, C$_{1-6}$ aminoalkyl, trifluomomethyl, hydroxy, C$_{1-6}$ alkoxy, aryloxy, keto, C$_{1-3}$ alkylenedioxy, nitro, cyano, carboxy, C$_{2-6}$ alkoxycarbonyl, C$_{2-6}$ alkoxycarbonyl(C$_{1-6}$)alkyl, C$_{2-6}$ alkylcarbonyloxy, arylcarbonyloxy, aminocarbonyloxy, C$_{2-6}$ alkylcarbonyl, arylcarbonyl, C$_{1-6}$ alkylthio, C$_{1-6}$ alkylsulphinyl, C$_{1-6}$ alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$NR$^v$R$^w$ and —CH$_2$SO$_2$NR$^v$R$^w$, in which R$^v$ and R$^w$ independently represent hydrogen, C$_{1-6}$ alkyl, aryl or aryl(C$_{1-6}$)alkyl, and Aryl is pheny or naphthyl.

2. A compound as claimed in claim 1 represented by formula IIA, or a pharmaceutically acceptable salt thereof:

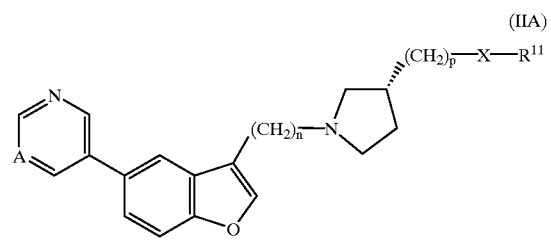

wherein n is 2,3 or 4;

p is zero, 1 or 2;

A represents C—R$^5$;

R$^5$ represents hydrogen, C$_{2-4}$ alkoxycarbonyl, C$_{1-3}$ alkoxy (C$_{1-3}$)alkyl or C$_{1-3}$ alkylsulphonylamino(C$_{1-3}$)alkyl;

X represents oxygen, sulphur, —SO—, —SO$_2$— or N—R$^{12}$; and

R$^{11}$ and R$^{12}$ independently represent hydrogen, C$_{1-6}$ alkyl, C$_{2-6}$ alkenyl, C$_{3-7}$ cycloalkyl(C$_{1-6}$)alkyl, indanyl, aryl, or aryl(C$_{1-6}$)alkyl, any of which groups may be optionally substituted with one or more substitutuents independently selected from C$_{1-6}$ alkyl, halogen, cyano, trifuoromethyl, hydroxy, C$_{1-6}$ alkoxy, aminocarbonyloxy, C$_{2-6}$ alkylcarbonyl, amino, C$_{1-6}$ alkylamino, di(C$_{1-6}$)alkylamino, C$_{2-6}$ alkylcarbonylamino, C$_{1-6}$ alkylsulphonylamino and C$_{1-6}$ alkylaminosulphonylmethyl.

3. The compound:

N-methyl-N-[(1S)-1-phenylethyl]-N-[(3R)-1-(2-(5-(pyridin-3-yl)benzofuran-3-yl)ethyl)pyrrolidin-3-ylmethyl]amine or a pharmaceutically acceptable salt thereof.

4. A pharmaceutical composition comprising a compound of formula I as defined in claim 1 or a pharmaceutically acceptable salt thereof in association with a pharmaceutically acceptable carrier.

5. A method for the treatment of migraine, cluster headache, chronic paroxysmal hemicrania, headache associated with vascular disorders, tension headache, and pediatric migraine, which method comprises administering to a patient in need of such treatment an effective amount of a compound of formula I as defined in claim 1 or a pharmaceutically acceptable salt thereof.

* * * * *